(12) United States Patent
Mande et al.

(10) Patent No.: US 11,735,289 B2
(45) Date of Patent: Aug. 22, 2023

(54) METHOD AND SYSTEM FOR ANALYZING METABOLIC STATE OF A CELL BY MEASURING CONCENTRATIONS OF METABOLITES

(71) Applicant: Tata Consultancy Services Limited, Mumbai (IN)

(72) Inventors: Sharmila Shekhar Mande, Pune (IN); Arvind J Shankar, Pune (IN); Tungadri Bose, Pune (IN); Anirban Dutta, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 1120 days.

(21) Appl. No.: 16/249,620

(22) Filed: Jan. 16, 2019

(65) Prior Publication Data
US 2019/0221282 A1    Jul. 18, 2019

(30) Foreign Application Priority Data
Jan. 18, 2018 (IN) .............................. 201821002156

(51) Int. Cl.
*G01N 33/48* (2006.01)
*G16B 5/20* (2019.01)
*G16B 5/00* (2019.01)

(52) U.S. Cl.
CPC ................ *G16B 5/20* (2019.02); *G16B 5/00* (2019.02)

(58) Field of Classification Search
None
See application file for complete search history.

(56) References Cited

U.S. PATENT DOCUMENTS

| | | | |
|---|---|---|---|
| 8,086,414 B2 | 12/2011 | Maranas et al. | |
| 8,301,393 B2 | 10/2012 | Palsson et al. | |
| 8,510,054 B2 | 8/2013 | Iwatani et al. | |
| 2019/0367930 A1* | 12/2019 | Li | C12N 15/52 |

OTHER PUBLICATIONS

Orth, Jeffrey D., Ines Thiele, and Bernhard Ø. Palsson. "What is flux balance analysis?." Nature biotechnology 28.3 (2010): 245-248.*
Opdam, Sjoerd, et al. "A systematic evaluation of methods for tailoring genome-scale metabolic models." Cell systems 4.3 (2017): 318-329.*

* cited by examiner

*Primary Examiner* — Anna Skibinsky
(74) *Attorney, Agent, or Firm* — Finnegan, Henderson, Farabow, Garrett & Dunner LLP

(57) ABSTRACT

Analysis of the flow of fluxes through the metabolic network of a cell type is useful in gaining knowledge about cellular physiology. Such knowledge can be used in understanding host's interactions with pathogens, drug response etc. However there is dearth of techniques that can incorporate metabolomics data into genome scale metabolic model (GEM) for FBA. A method and system for analyzing metabolic state of a cell at a genome scale by measuring concentrations of a one or more metabolites has been disclosed. The method is utilizing intracellular and/or extracellular metabolite concentrations for constraining reaction fluxes in FBA by incorporating it as part of stoichiometric constraint to metabolic model. The method is used to predict the change in flux flow through all reactions in an organism/cell type under different experimental conditions. The method enables constraining the flow of fluxes through reactions while performing FBA of GEMs using measured metabolite concentrations.

8 Claims, 3 Drawing Sheets

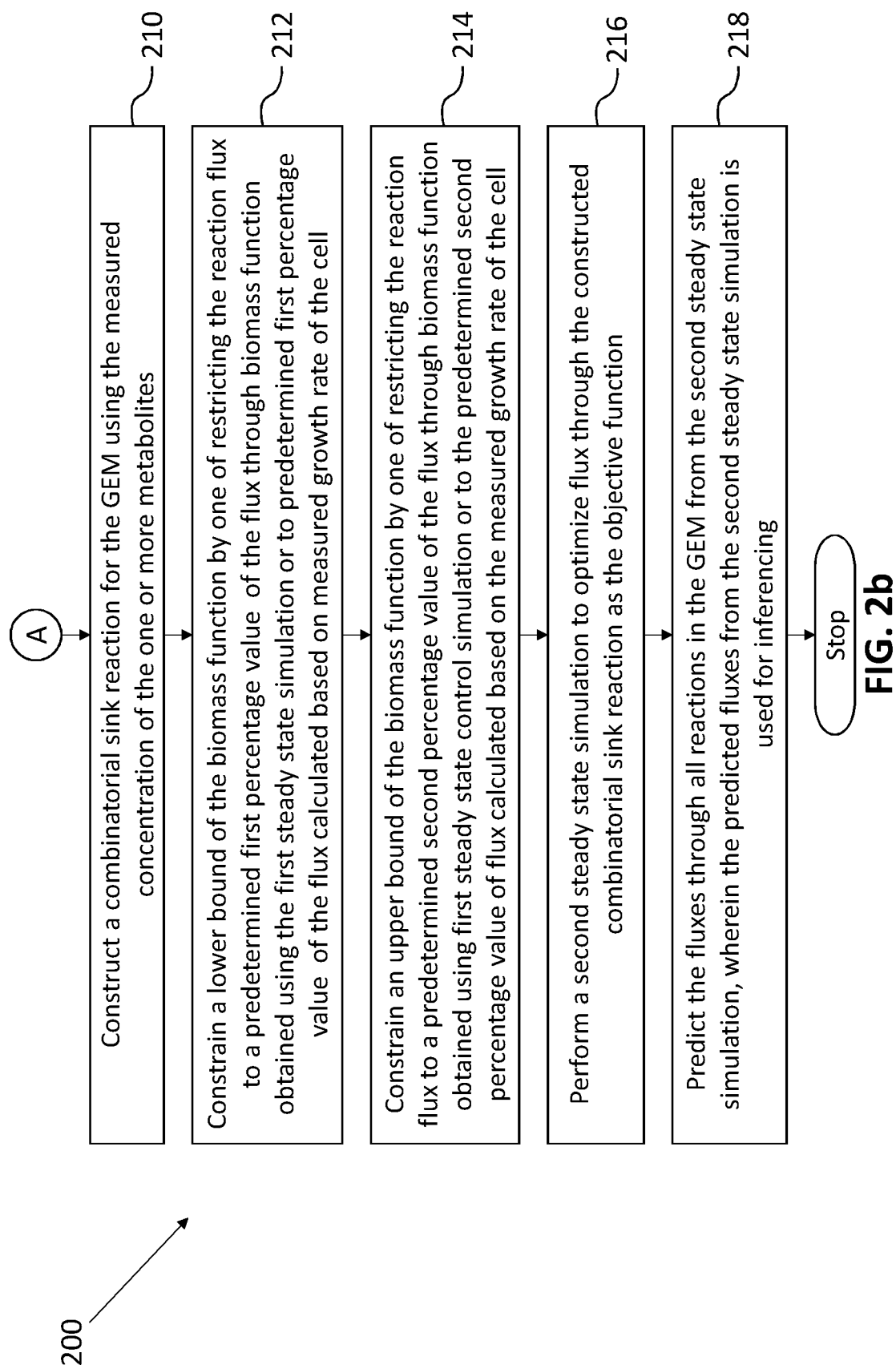

METHOD AND SYSTEM FOR ANALYZING METABOLIC STATE OF A CELL BY MEASURING CONCENTRATIONS OF METABOLITES

PRIORITY CLAIM

This U.S. patent application claims priority under 35 U.S.C. § 119 to: India Application No. 201821002156, filed on 18 Jan. 2018. The entire contents of the aforementioned application are incorporated herein by reference.

TECHNICAL FIELD

The disclosure herein generally relates to the field of computational prediction of fluxomics and, more particularly, to method and system for analyzing metabolic state of a cell at a genome scale by measuring concentrations of a one or more metabolites.

BACKGROUND

An ever growing body of evidence in biology seems to suggest the role of altered cell metabolism in disease. Further, most organism/cell types are known to undergo specific changes in metabolism to adapt to its environment. Analysis of the flow of fluxes through the metabolic network of an organism/cell type may be useful in identifying the key regulatory nodes which help in understanding normal and pathological cell physiology, thereby aiding in target identification for rational drug-design. In addition, better understanding of alteration of metabolic fluxes and their relationship with nutrient-availability, as well as other environmental conditions, can guide in strain improvement of industrially important microbes.

Estimation of genome scale metabolic reaction fluxes through experiments (also referred to as fluxomics) entail the use of highly sophisticated analytical techniques such as, mass spectroscopy (MS), ultra-performance liquid chromatography (UPLC), and/or nuclear magnetic resonance (NMR) as well as very expensive (radio-labelled) tracer compounds. Apart from being expensive, interpretation of results from such experiments involves complex mathematical treatise. Consequently, researchers have developed computational methods to overcome the challenges of fluxomic analysis.

Flux Balance Analysis (FBA) is usually employed to predict either the effect (change in metabolic flux through reactions) of (a) changes in the growth/experimental conditions (such as, alterations in the composition of the media used to grow an organism) or (b) knocking out (or blocking) one or more enzyme encoding genes (or proteins) and/or incorporating new enzyme encoding gene(s) on the overall distribution of reaction fluxes in an organism/cell type/ensemble of dissimilar cell types using Genome-scale Metabolic models (GEMs). However, results obtained through such simulations are often seen to predict fluxes beyond biologically meaningful ranges for certain reactions. Subsequently, researchers have proposed methods for using omics (transcriptomic/metabolomics) data to constrain reactions into biologically meaningful ranges.

There are few methods which involve constrainment of metabolic flux through GEMs using either of transcriptomic data or metabolomics data (or thermodynamic constraints). But these methods have several limitations and often fail to replicate experimentally observed metabolic fluxes. Although methods for constrained FBA using transcriptomic data provide results more comparable to the experimental data (against unconstrained FBA), it still fails to capture the effects of thermodynamic constraints and law of mass action which determine the flow of flux through reactions. Further, especially for eukaryotic systems, wherein most proteins undergo post translational modifications, transcriptomic levels cannot be equated to protein (enzyme) levels and thus constrained FBA using transcriptomic data is not applicable.

Existing methods of integrating metabolomics data (metabolite concentration) with GEMs for FBA suffer from many gaps in knowledge as well as techniques used. Till date, there are no standardized methodology/technique for directly integrating metabolite concentration data and is an active field of research.

Thermodynamic constraints may be applied to metabolic networks based on estimation of Gibbs free energy from the measured metabolite concentrations. Gibbs free energy is helpful in ascertaining the directionality of the flow of fluxes through the reactions. Knowledge pertaining to the concentrations of all the reactants and the products as well as the experimental condition (temperature) is essential for calculating the Gibbs free energy. However, state-of-the-art infrastructure allows measurement of the concentrations of only 50 to 200 metabolites from a pool of over 1000 metabolites which typically constitute the metabolome of a cell (or a multitude of similar/dissimilar cell types). Therefore the obtained metabolomics data is inadequate for computing the Gibbs free energy for most reactions in the organism/cell types.

To overcome the above limitation, most biologists design their experiments to only measure the metabolite concentrations from the central carbon metabolic pathways. In that case, the thermodynamic approaches to constrain FBA may be applied. However, the constrainment can only be applied to the subset of reactions representing central carbon metabolism and not to the entire genome scale network. Ancillary reactions, other than those constituting the central carbon metabolism largely remain unconstrained. Further, unsteady state flux balance assumptions allow the use of metabolite concentrations for constraining fluxes through GEMs, but require time-course metabolite concentration data (at least two time points) for the constrainment.

SUMMARY

Embodiments of the present disclosure present technological improvements as solutions to one or more of the above-mentioned technical problems recognized by the inventors in conventional systems. For example, in one embodiment, a system for analyzing metabolic state of a cell/ensemble of cells at a genome scale by measuring concentrations of one or more metabolites is provided. The system comprises a metabolite concentration measurement tool, a growth rate measurement tool, a memory and a processor in communication with the memory. The metabolite concentration measurement tool measures a concentration of the one or more metabolites present in the cell and the cell culture. The growth rate measurement tool measures a growth rate of the cell in the cell culture. The processor further comprises a model creation module, a first simulation module, a sink reaction construction module, an input module, a second simulation module and a flux prediction module. The model creation module creates a genome scale metabolic model (GEM) for the cell(s) using genomic information of the cellular organism(s), wherein the model is using a biomass function as an objective function. The first simulation module performs a first steady state simulation of the GEM while optimizing flux through biomass function by applying only minimal constraints on reaction fluxes, wherein the minimal constraints are based on predefined input parameters, and wherein simulation results pertain to steady state flux values through all reactions in the GEM. The sink reaction construction module constructs a combinatorial sink reaction for the GEM using the measured concentration of the one or more metabolites. The input module constrains a lower bound of the biomass function by one of restricting the reaction flux to a predetermined first percentage value of the flux through biomass function obtained using the first steady state simulation or to the predetermined first percentage value of the flux calculated based on measured growth rate of the cell(s). The input module also constrains an upper bound of the biomass function by one of restricting the reaction flux to a predetermined second percentage value of the flux through biomass function obtained using the first steady state control simulation or to the predetermined second percentage value of the flux calculated based on the measured growth rate of the cell(s). The second simulation module performs a second steady state simulation to optimize flux through the constructed combinatorial sink reaction as the objective function. The flux prediction module predicts the fluxes through all reactions in the GEM from the second steady state simulation, wherein the predicted fluxes from the second steady state simulation is used for inferencing.

In another embodiment, a method for analyzing metabolic state of a cell at a genome scale by measuring concentrations of a one or more metabolites is provided. Initially, a concentration of the one or more metabolites present in the cell and the cell culture are measured. A growth rate of the cell in the cell culture is also measured. In the next step, a genome scale metabolic model (GEM) for the cell is created using genomic information of the cellular organism, wherein the model is using a biomass function as an objective function. In the next step, a first steady state simulation of the GEM is performed while optimizing flux through biomass function by applying only minimal constraints on reaction fluxes, wherein the minimal constraints are based on predefined input parameters, and wherein simulation results pertain to steady state flux values through all reactions in the GEM. In the next step, a combinatorial sink reaction for the GEM is constructed using the measured concentration of the one or more metabolites. In the next step, a lower bound of the biomass function is constraint by one of restricting the reaction flux to a predetermined first percentage value of the flux through biomass function obtained using the first steady state simulation or to the predetermined first percentage value of the flux calculated based on measured growth rate of the cell(s). Similarly, the upper bound of the biomass function is constraint by one of restricting the reaction flux to a predetermined second percentage value of the flux through biomass function obtained using the first steady state control simulation or to the predetermined second percentage value of the flux calculated based on the measured growth rate of the cell(s). In the next step, a second steady state simulation is performed to optimize flux through the constructed combinatorial sink reaction as the objective function. And finally, the fluxes through all reactions in the GEM is predicted from the second steady state simulation, wherein the predicted fluxes from the second steady state simulation is used for inferencing.

In yet another embodiment, One or more non-transitory machine readable information storage mediums comprising one or more instructions which when executed by one or more hardware processors cause as follows. Initially, a concentration of the one or more metabolites present in the cell and the cell culture are measured. A growth rate of the cell in the cell culture is also measured. In the next step, a genome scale metabolic model (GEM) for the cell is created using genomic information of the cellular organism, wherein the model is using a biomass function as an objective function. In the next step, a first steady state simulation of the GEM is performed while optimizing flux through biomass function by applying only minimal constraints on reaction fluxes, wherein the minimal constraints are based on predefined input parameters, and wherein simulation results pertain to steady state flux values through all reactions in the GEM. In the next step, a combinatorial sink reaction for the GEM is constructed using the measured concentration of the one or more metabolites. In the next step, a lower bound of the biomass function is constraint by one of restricting the reaction flux to a predetermined first percentage value of the flux through biomass function obtained using the first steady state simulation or to the predetermined first percentage value of the flux calculated based on measured growth rate of the cell(s). Similarly, the upper bound of the biomass function is constraint by one of restricting the reaction flux to a predetermined second percentage value of the flux through biomass function obtained using the first steady state control simulation or to the predetermined second percentage value of the flux calculated based on the measured growth rate of the cell(s). In the next step, a second steady state simulation is performed to optimize flux through the constructed combinatorial sink reaction as the objective function. And finally, the fluxes through all reactions in the GEM is predicted from the second steady state simulation, wherein the predicted fluxes from the second steady state simulation is used for inferencing.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 2A-2B is a flow diagram illustrating steps involved in the analyzing metabolic state of a cell at a genome scale by measuring concentrations of a one or more metabolites according to an embodiment of the present disclosure.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Glossary—Terms Used in the Embodiments

The expression "Genome Scale Metabolic Model" or "GEMs" in the context of the present disclosure refers to an ensemble of chemical reactions that take place inside a living organism/cell type/aggregation of dissimilar cell types. It is reconstructed based on genomic potential of the organism/cell type(s) as well as information available in literature. Genomic potential of the organism/cell type(s), in this case, may be considered as the set of enzymes which the organism/cell type(s) encode in the genome, wherein the said enzymes either alone or together with other enzymes/co-factors could catalyze one or more chemical reactions.

The expression "Flux Balance Analysis" or "FBA" in the context of the present disclosure refers to an approach to analyze the flow of metabolites through a metabolic network. FBA uses mathematical principles to gauge the flow of metabolic fluxes through different reactions in a metabolic network. It has been explained in detail in the later part of the disclosure.

Figure 1:
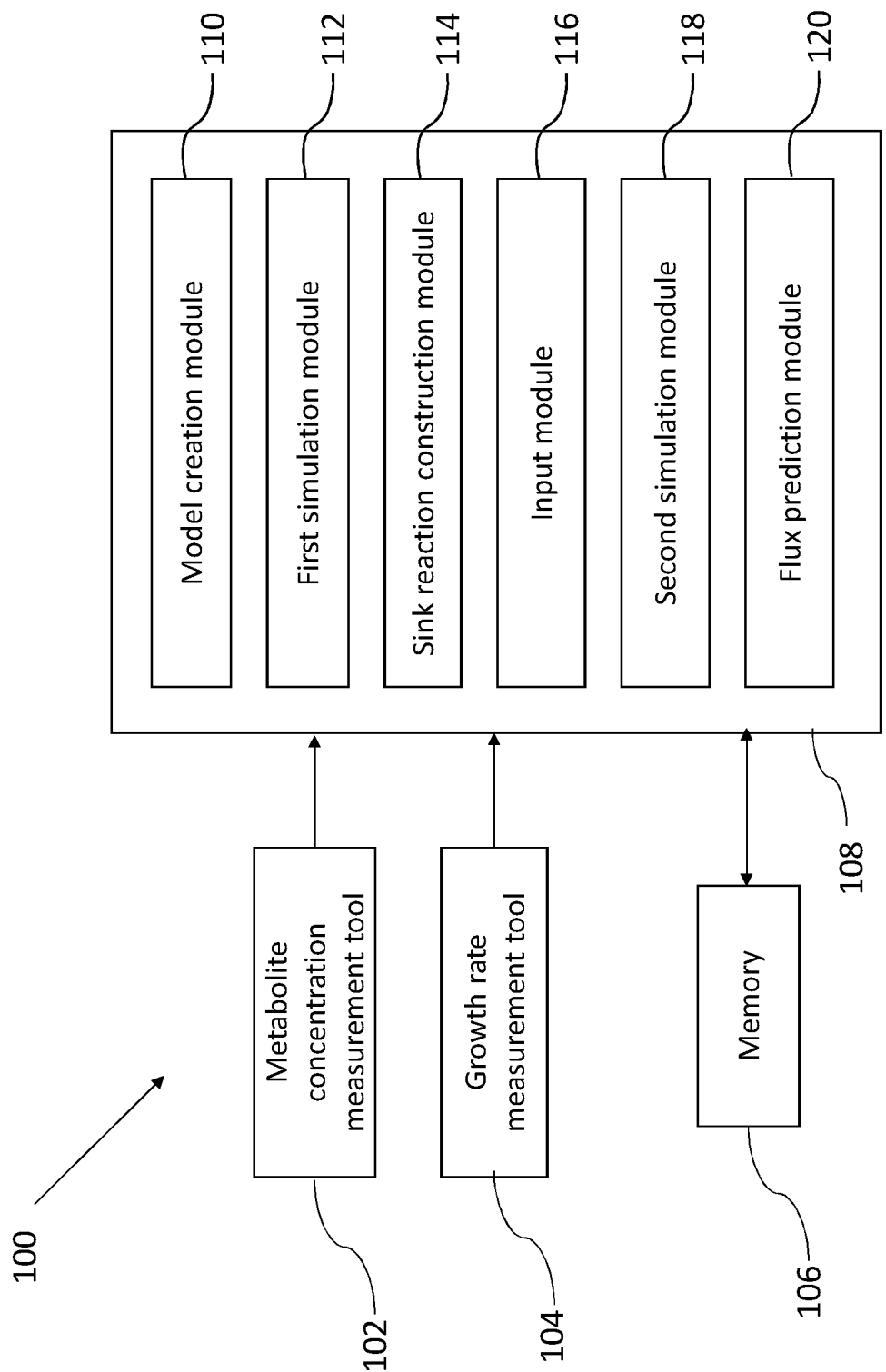
FIG. 1 is a functional block diagram of a system for analyzing metabolic state of a cell at a genome scale by measuring concentrations of a one or more metabolites according to an embodiment of the present disclosure.
Figure 2A:
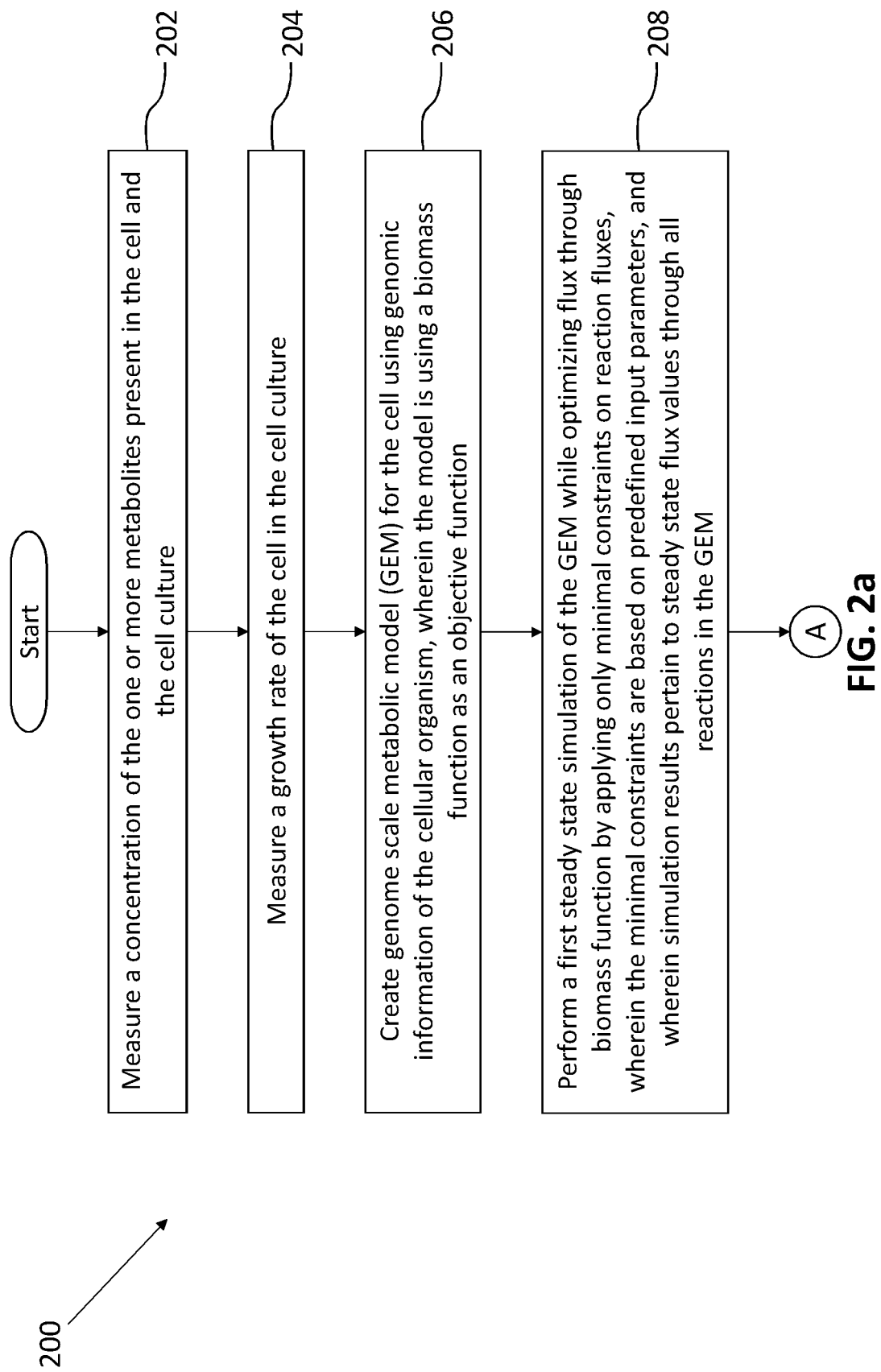

Referring now to the drawings, and more particularly to FIG. 1 through FIG. 2, where similar reference characters denote corresponding features consistently throughout the figures, there are shown preferred embodiments and these embodiments are described in the context of the following exemplary system and/or method.

According to an embodiment of the disclosure, a system 100 for analyzing metabolic state of cell(s) at a genome scale by measuring concentrations of a one or more metabolites is shown in the block diagram of FIG. 1. The system is used to predict the change in flow of flux through all reactions in an organism/cell type(s) under different experimental/growth conditions. The system 100 uses static/time-course intracellular and/or extracellular metabolite concentration measurements and incorporate them into GEMs for performing FBA. Constraining of fluxes based on metabolite concentrations, using the proposed approach, improves prediction of reaction fluxes compared to a classical FBA, wherein no (or limited) constraints are used to bind the reaction fluxes to biologically meaningful ranges.

It should be appreciated that the system 100 requires a model resembling a sub-system or a pathway within the cell. In an embodiment the genome scale metabolic model (GEM) has been used. In addition to representing the metabolic potential of a single organism (like a bacterial cell), the GEM can also represent a smaller sub-system of enzymatic reactions from the organism. Additionally, it can also represent the metabolic potential of an ensemble of similar cells which might demonstrate alternate phenotypes (like variations in phases of cell cycle, metabolism, stress resistance, etc.). It should be appreciated that the GEM may be an amalgamation of multiple genome scale models representing a microbiome or metabolic exchanges of the organism/microbiota with the host, etc. This can be done for even smaller scale metabolic networks, and can in principle be extended to multi-genome networks.

Flux Balance analysis is a mathematical approach to determine steady state flux distributions of metabolic networks derived from genome sequence i.e. it calculates the flow of metabolites through a biochemical network. They provide a prediction of growth rates and product secretion rates in the absence of kinetic parameters and experimental technology deficit. It is based on two assumptions. I. Steady State: There is no net change in concentration of metabolites over time, as metabolites are produced and consumed by in equal proportions by the reactions in the system. II. Optimality: Biological systems under evolutionary pressure are optimized for some biological objective such as biomass production, energy conservation, metabolite secretion etc. The stoichiometric coefficients of all the reactions in the model are converted into a system of linear equations subject to which a biological objective is optimized. This can be represented in a matrix[S] form of size m×n, with m metabolites and n reactions with most of the values in the matrix being 0 since only the reactions that have the metabolites participating in them have stoichiometric coefficients as non-zero values.

All the reactions in the model are mass balanced and its stoichiometry forms the constraints subject to which the system is optimized for a biological objective such as growth. In addition to stoichiometric constraints on metabolite utilization, the maximal and minimal flux through all reactions is constrained to biologically realizable limits. Thus under steady state assumptions, it becomes a linear programming problem with linear constraints. Mathematical representation of the Flux Balance analysis can be provided as follows:

Optimize objective function $Z=\Sigma_{i=1}^{i=n} c_i \cdot v_i = C_t \cdot V$

Subject to $S \cdot V = 0$

And $v_{min} <= v_i <= v_{max}$

Where C is a vector of weights
V is a vector of fluxes
S is the stoichiometric matrix of size m×n
m is the number of metabolites
and n is the number of reactions According to an embodiment of the disclosure, the system 100 comprises of a metabolite concentration measurement tool 102, a growth rate measurement tool 104, a memory 106 and a processor 108 in communication with the memory 106 as shown in the block diagram of FIG. 1. The processor 108 configured to execute a plurality of algorithms stored in the memory 106. The processor 108 further includes a plurality of modules for performing various functions. The processor 108 may include a model creation module 110, a first simulation module 112, a sink reaction construction module 114, an input module (or constrainment module) 116, a second simulation module 118 and a flux prediction module 120.

The system 100 can be explained with the help of optimization or constrainment of any reaction in the genome-scale metabolic model. In an example, a biomass reaction has been used. Depending on the purpose of the experiment, reactions other than the biomass reaction maybe optimized or constrained. For example, if the purpose of the experiment is to check the effect of different carbon sources (nutrients) on the production of certain industrially relevant compounds (such as, ethanol, insulin, etc.), then the GEM may be appropriately modified (by including one or more reactions) and one or more reaction(s) may be appropriate constrained based on experimental observations.

According to an embodiment of the disclosure, the system 100 comprises the metabolite concentration measurement tool 102. The metabolite concentration measurement tool 102 is employed for measuring the concentrations of the intracellular/extracellular metabolites from cell cultures, using standard laboratory protocols. The metabolite concentration measurement tool 102 measures concentration of the one or more metabolites present in the cell and the cell culture. The cell is one of a eukaryotic cell or a prokaryotic cell. It should be appreciated that any other living cell or a user defined compartment(s) or aggregation of cells wherein a multitude of metabolic reactions are going on simultaneously can also be used. Further, it should be appreciated that not all the metabolites in the cell needs to be measured. Any appropriate subset of the plurality of metabolites in a cell may be measured for use with this method. In another embodiment, the GEMs of multiple organisms/cell types (such as those constituting a microbiome) may be combined to form a super model and the proposed invention may be implemented on the obtained super model.

In one implementation the metabolites may be measured using a known variant of mass spectrometry such as Quadrupole time-of-flight mass spectrometry (Q-Tof), liquid chromatography-mass spectrometric multiple reaction monitoring (LC-MRM/MS), etc. In alternate implementations the metabolites may be measured using other analytical techniques such as chromatography, spectrophotometry, circular dichroism, etc. The measured metabolite concentration is to be converted into mM (milli Molar) units (using standard conversion techniques) for integration into the GEM.

According to an embodiment of the disclosure, the system 100 further comprises the growth rate measurement tool 104. The growth rate measurement tool 104 is equipped to quantify/interpret the growth rate of cells in the cell culture from the optical density (OD) of the cell culture, wherein the OD is measured using spectrophotometry (or a similar technique). Alternately, it may be measured from the knowledge of cell doubling rate obtained from instruments such as a cell counter, or through microscopic methods, or cytometers or literature. In another embodiment of the proposed method, one or more of alternate physically measureable parameters (such as cell wall thickness, secondary metabolite production, etc.), either alone or along with the growth rate, may be used for constraining of flux through the GEM.

According to an embodiment of the disclosure, the processor 108 further comprises the model creation module 110. The model creation module 110 is configured to create the genome scale metabolic model (GEM) for the cell using genomic information of the cellular organism, wherein the model is using a biomass function as an objective function. This module is configured to obtain the GEM of the organism/cell type(s) to be studied using FBA. In an example if case a previously build model is not available (or only an incomplete model is available); the GEM of the organism/cell type(s) may be created from the genomic data of the organism/cell type(s). Depending on the purpose of the experiment, reactions other than the biomass reaction may also be constrained. For example, if the purpose of the experiment is to check the effect of different carbon sources (nutrients) on the production of certain industrially relevant compounds (such as, ethanol, insulin, etc.), then the GEM may be appropriately modified (by including one or more reactions) and one or more reaction(s) may be appropriate constrained based on experimental observations.

According to an embodiment of the disclosure, the processor 108 comprises the first simulation module 112. The first simulation module 112 is configured to perform a first steady state simulation of the GEM while optimizing flux through biomass function by applying only minimal constraints on reaction fluxes, wherein the minimal constraints are based on predefined input parameters (such as available type and concentration of nutrients, pH, oxygen availability, antimicrobial treatment, etc.), and wherein simulation results pertain to steady state flux values through all reactions in the GEM. The simulation is performed such that the simulation results could mimic the experimental conditions (for example, nutrient availability, pH, oxygen availability, antimicrobial treatment, etc.).

According to an embodiment of the disclosure, the processor 108 further comprises the sink reaction construction module 114. The sink reaction construction module 114 is configured to construct a combinatorial sink reaction for the GEM using the measured concentration of the one or more metabolites. The mathematical representation of the combinatorial sink function derived from metabolite concentration is given below:

$$v_{accum} = \sum_{i=1}^{m} c_i m_i$$

Where, m is the number of metabolite concentrations measured $m^e$ M where M is all the produced metabolites present in the network $c_i$ is the concentration of the metabolite measured (in mM units)

$v_{accum}$ is a sink function that will be the new objective to reconcile metabolic measurements The function of this module is to use the union of metabolites measured and those present in the model for constructing the combinatorial sink reaction, wherein the metabolites are used in a stoichiometric ratio equivalent to their normalized measured concentrations (in mM units). The sink functions may be created from the metabolite concentration data obtained under control and one or more test experimental condition. The sink functions are to be appropriately added to the GEM.

The measured concentrations are normalized to cell count/or dry cell weight and converted into mM units, which are then used as the stoichiometric coefficients of the metabolites. In case of relative measurements of metabolite concentrations with multiple samples, the absolute concentrations as required for the construction of the sink function maybe estimated with literature sources or a standard measurement of at least one of the samples. The standard measurement may be obtained for one of the metabolites from the central carbon metabolism (such as pyruvate or oxaloacetate) or a metabolite of physiological importance (such as a nucleotide like adenosine, amino acids like glutamate, fatty acids like butyrate, etc.).

This sink function is to be used as the new objective function which will implicitly constrain any successive simulation subject to growth rate and nutrient uptake conditions. The mathematical formulation for the same inspired by Flux balance analysis is as follows:

Maximize $Z = v_{accum}$

Subject to Maximize $V_{lb,biomass} = V_{biomass}*$ for $gr$

Subject to $S \cdot V = 0$ $lb <= v_i <= ub$ where $v_{accum}$ is the flux through constructed sink function
$v_{lb,biomass}$ is the lower bound of the biomass flux vector
$v_{biomass}$ is the biomass flux vector approximating growth rate
$gr$ is the experimentally measured growth rate f is the fraction of growth rate relaxation (based on experimental "or" theoretical data)

According to an embodiment of the disclosure, the system 100 further comprises the input module 116 and the second simulation module 118. The input module 116 may also be referred the constraining module 116. The input module 116 is configured to constraint the biomass function. A lower bound of the biomass function is constraint by one of restricting the reaction flux to a predetermined first percentage value of the flux through biomass function obtained using the first steady state simulation or to the predetermined first percentage value of the flux calculated based on measured growth rate of the cell(s). It should be appreciated that the value of the predetermined first percentage value is about 90% in an embodiment.

Similarly, the input module 116 also constrain an upper bound. The upper bound of the biomass function is constraint by one of restricting the reaction flux to a predetermined second percentage value of the flux through biomass function obtained using the first steady state control simulation or to the predetermined second percentage value of the flux calculated based on the measured growth rate of the cell(s). It should be appreciated that the value of the predetermined second percentage value is about 110% in an embodiment Further, the second simulation module 118 is configured to perform a second steady state simulation to optimize flux through the constructed combinatorial sink reaction as the objective function.

According to an embodiment of the disclosure, the processor 108 further comprises the flux prediction module 120. The flux prediction module 120 is configured to predict the fluxes through all reactions in the GEM from the second steady state simulation, wherein the predicted fluxes from the second steady state simulation is used for inferencing. The inferencing could be done for various applications including optimization of the yield of biotechnological or pharmaceutical compound, checking the effect of stress or therapeutics or spike-in of cells, analyzing metabolic changes on alternate use of nutrients, etc. The flux predictions are more accurate in reflecting metabolic state of a biological system as compared to any known methods of FBA.

According to an embodiment of the disclosure, the system 100 can also be used in a test condition and a control condition. In this case, the lower bound of the biomass function is constrained for the test condition and the control condition. The bound is depending on the value of a factor, wherein the factor is equivalent to the ratio of growth rates obtained under the test condition and the control condition. The value of the factor decides the constraint. First, if the factor is greater than one, then the lower bound is constrained by dividing the steady state flux value by the factor. Second, if the value is less than one then the lower bound is to be constrained by multiplying the steady state flux value by the factor. And third, if the factor is equal to one, then the lower bound is constrained to the predefined first percentage value of the steady state flux.

In operation, a flowchart 200 illustrating a method for analyzing metabolic state of cell(s) at a genome scale by measuring concentrations of a one or more metabolites. Initially at step 202, the concentration of the one or more metabolites present in the cell and the cell culture is measured. And at step 204, the growth rate of the cell(s) in the cell culture is measured. In the next step 206, the genome scale metabolic model (GEM) is created for the cell using genomic information of the cellular organism, wherein the model is using a biomass function as an objective function.

In the next step 208, the first steady state simulation of the GEM while optimizing flux through biomass function by applying only minimal constraints on reaction fluxes, wherein the minimal constraints are based on predefined input parameters, and wherein simulation results pertain to steady state flux values through all reactions in the GEM. At step 210, the combinatorial sink reaction for the GEM is constructed using the measured concentration of the one or more metabolites.

In the next step 212, the lower bound of the biomass function is constraint by one of restricting the reaction flux to the predefined first percentage value of the flux through biomass function obtained using the first steady state simulation or to the predefined first percentage value of the flux calculated based on measured growth rate of the cell(s). Similarly, at step 214, the upper bound of the biomass function by one of restricting the reaction flux to the predefined second percentage value of the flux through biomass function obtained using the first steady state control simulation or to the predefined second percentage value of the flux calculated based on the measured growth rate of the cell(s).

In the next step 216, the second steady state simulation is performed to optimize flux through the constructed combinatorial sink reaction as the objective function. And finally at step 218, the fluxes through all reactions in the GEM are predicted from the second steady state simulation, wherein the predicted fluxes from the second steady state simulation is used for inferencing. The inferencing could be done for various biotechnological and pharmaceutical applications.

According to an embodiment of the disclosure, the proposed method does not have the shortcoming associated with the unsteady state assumptions. This allows the simulation to be formulated as a linear programming problem as compared to the unsteady state approach, wherein the method to constrain flux through reactions involve prediction/use of any kinetic parameters which are often compute intensive.

According to an embodiment of the disclosure, the system 100 may also be applied to a subset of reactions or to a set of reactions pertaining to one or more metabolic pathways, instead of the whole genome scale metabolic model. In another embodiment, the GEMs of multiple organisms/cell types may be combined to form a super model and the proposed disclosure may be implemented on the obtained supermodel.

In another example, if the data pertaining to only a single experimental condition is available (and that for independent control and test conditions are not available), the method may be employed to infer the flow of flux through that experimental condition as well. The sink reaction is designed based on the metabolic accumulation data while constraining the biomass reaction to 90% of steady state flux if actual growth rate of the cells are not available. If actual growth rate is available, the same may also be used for constraining the biomass reaction. In another implementation corresponding to the above scenario, a single simulation may be run, wherein a new objective function is implemented, which maximizes the summation of flux through the biomass function and the combinatorial sink function.

In another embodiment of the disclosure, the proposed method may be augmented with additional flux constrainment techniques to improve the accuracy of prediction of the reaction fluxes. For example, the additional flux constraining may be based on at least one of genomic data, transcriptomic data, proteomic data, lipidomic data, glycomic data, amplicon sequencing data, whole (meta) genome sequencing data, nutritional data, pharmacological data, toxicological data, thermodynamic constrains, and time-course metabolic data, etc.

According to an embodiment of the disclosure, the genome scale metabolic model can be built as explained below. A complete genome scale metabolic network contains all the reactions and metabolites involved in genome scale reconstructions are commonly used with Flux Balance Analysis and other constraint based methods to investigate metabolic potential. High quality genome sequencing and annotation together with biochemical and physiological data is required to construct accurate metabolic networks. A variety of databases exist, that contain various levels of biological information, this together with text mining and high quality reaction databases and enzyme sequence conservation allow to automatically reconstruct draft metabolic networks which then have to be further refined in a semi-automated or manual method for biological and factual accuracy. This rational approach to building genome scale network is now possible with the advent of high throughput sequencing that lead to an explosion of genome sequences of various organisms and annotation of proteins and enzymes that catalyze biochemical reactions that drive cell systems. The main steps involved to build a metabolic network/genome scale model/reconstruction are as follows:

a. Acquire genomic information. The genomic information is obtained from public databases like GenBank, EBI, DDBJ, etc.
b. Identify metabolic functions based on genome sequence annotation
c. Obtain generic reactions for metabolic functions
d. Assemble a draft biochemical network
e. Verify, prune and add reactions and gene reaction rules
f. Add spontaneous, exchange and demand reactions
g. Add biological objective function and test for gaps
h. Transform network into a computable model for simulations
i. Evaluate and test network properties According to an embodiment of the disclosure, the method and system can also be explained with the help of following experimental results. The method of incorporating metabolite concentrations as part of the stoichiometric constraints of metabolic models and the formulation of a new objective function abbreviated here as MetConc validated here with experimental data for $E.$ $coli$. Given the unavailability of proper implementations of methods to constrain genome wide metabolic flux through GEMs using metabolite concentration measurements, the proposed method is benchmarked against classical FBA and other existing methods that constrain FBA solutions based on other-omics (primarily transcriptomic) data. The flux values provided in the Table are expressed as percentage normalized ratios with respect to the glucose uptake rate.

| Reaction ID | Reactions Methods | Experimental Flux (%) | Predicted Fluxes with different methods (%) | | | | | | |
|---|---|---|---|---|---|---|---|---|---|
| | | | E-Fmin | GIMME | FBA (classical) | E-Flux | Lee | iMAT | Metconc |
| GLCptspp | Glucose + PEP -> G6P + PYR | 100.00 | 100.00 | 100.00 | 100.00 | 0.79 | 100.00 | 100.00 | 100.00 |
| PGI | G6P -> F6P | 62.20 | 33.40 | 36.50 | 87.04 | 0.79 | 99.40 | 4.78 | 62.98 |
| PFK | F6P -> F1.6P | 80.20 | 41.50 | 71.30 | 0.00 | 8.29 | 99.40 | 60.80 | 72.65 |
| FBA | F1.6P -> DHAP + G3P | 80.20 | 41.50 | 71.30 | 0.00 | 8.29 | 99.40 | 60.80 | 72.60 |
| TPI | DHAP -> GJP | 80.20 | 68.30 | 70.10 | 88.13 | 3.85 | 99.40 | 59.50 | 78.26 |
| PGK | GJP -> JPG | 167.00 | 155.00 | 158.00 | 177.72 | 24.00 | 199.00 | 148.00 | 165.63 |
| ENO | JPG -> FEP | 157.00 | 139.00 | 144.00 | 165.30 | 19.00 | 199.00 | 133.00 | 142.31 |
| PYK | FEP -> PYK | 52.90 | 0.00 | 23.40 | 0.00 | 0.00 | 50.10 | 0.00 | 0.00 |
| PDH | PYK -> ArCoA + CO2 | 136.00 | 101.00 | 97.80 | 0.00 | 17.20 | 0.00 | 75.40 | 84.28 |
| PGL | G6P -> 6PG | 36.30 | 66.60 | 63.50 | 12.96 | 0.00 | 0.63 | 95.20 | 36.81 |
| GND | 6PG -> RaSP + CO2 | 36.30 | 66.60 | 63.50 | 12.96 | 1.24 | 0.00 | 95.20 | 36.81 |
| RPE | Rn5P -> X5P | 18.70 | 37.10 | 35.60 | 2.85 | -3.81 | 0.00 | 56.80 | 17.64 |
| RPI | Rx5P -> R5P | 17.60 | 29.10 | 27.50 | 9.81 | 4.92 | 0.00 | 38.10 | 18.81 |
| TKT1 | R5P -> X5P -> S7P + G3P | 10.80 | 20.30 | 19.40 | 2.85 | -1.34 | 0.00 | 30.00 | 10.29 |
| TALA | S7P + G3P -> E4P + F6P | 10.80 | 20.30 | 19.40 | 2.85 | -1.34 | 0.00 | 30.00 | 10.23 |
| TKT2 | X5P + E4P -> F6P + G3P | 7.80 | 16.80 | 16.20 | 0.00 | -2.47 | 0.00 | 26.80 | 7.35 |
| CS | ArCoA + OAA -> CTT | 82.20 | 39.90 | 21.60 | 54.49 | 7.21 | 0.00 | 47.00 | 60.53 |
| ACONTa | CTT -> ICT | 82.20 | 39.90 | 21.60 | 54.49 | 7.21 | 0.00 | 47.00 | 60.53 |
| ICDH$_{yn}$ | ICT -> 2-KG + CO2 | 56.40 | 15.10 | 9.32 | 32.40 | 3.26 | 0.00 | 47.00 | 60.53 |
| AKGDH | 2-KG -> SUC + CO2 | 48.10 | 0.00 | -4.55 | 24.38 | -1.59 | 0.00 | 100000* | 46.73 |
| SUCDi | SUC -> FUM | 73.90 | 29.80 | 12.30 | 46.48 | 3.94 | 0.00 | 37.70 | 46.70 |
| FUM | FUM -> MAL | 73.90 | 39.60 | 21.30 | 54.25 | 35.70 | 0.00 | 46.70 | 56.10 |
| MDH | MAL -> OAA | 95.50 | 64.40 | 33.70 | 76.34 | 39.60 | -24.40 | 46.70 | 56.12 |
| PPC | PEP + CO2 -> OAA | 0.20 | 3.22 | 13.30 | 0.00 | 5.04 | 49.30 | 25.60 | 29.10 |
| ME1 | MAL -> PYE + CO2 | 4.10 | 0.00 | 0.00 | 0.00 | 0.00 | 24.40 | 0.00 | 0.00 |
| ACKr | ArCoA -> Acetate | 0.00 | 0.00 | 31.40 | 30.91 | -1.76 | 31.40 | -5.04 | 0.00 |
| LDH_D | PYK -> Lactate | 0.00 | 0.00 | 0.00 | 0.00 | -14.70 | 200.00 | 0.00 | 0.00 |
| ALCD2x | ArCoA -> Ethanol | 0.00 | 0.00 | 0.00 | 0.00 | 0.00 | 0.00 | 0.00 | 0.00 |
| EX_co2_e | CO2 -> (Evalution) | 281.00 | 203.00 | 172.00 | 219.85 | 22.00 | 0.00 | 245.00 | 215.73 |
| RMSD | Root Mean square deviation | | 31.61 | 37.76 | 45.79 | 79.47 | 81.87 | 33.15 | 20.59 |

*Outliers with noisy predictions excluded from RMSD calculation $$\sqrt{\frac{\sum (P-E)2}{n}}$$

where, P is the predicted flux and E is the experimentally obtained flux through a reaction and n is the total number of reactions.

The overall RMSD values indicate superior performance of MetConc, as compared to the existing methods to constrain metabolic flux in GEMs. In other words, the metabolic fluxes through reactions, as predicted by MetConc are closer to the experimentally obtained values, as compared to other available methods. The simulation results are based on *E. coli* model.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein solves the problems of existing models for performing FBA. The disclosure provides a method and system for analyzing metabolic state of a cell at a genome scale by measuring concentrations of a one or more metabolites.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method for analyzing metabolic state of a cell at a genome scale by measuring concentrations of a one or more metabolites, the method comprising:

measuring a concentration of the one or more metabolites present in the cell and the cell culture by Quadrupole time-of-flight mass spectrometry (Q-Tof), liquid chromatography-mass spectrometric multiple reaction monitoring (LC-MRM/MS), nuclear magnetic resonance (NMR), ultra-performance liquid chromatography (UPLC), spectrophotometry, or circular dichroism;

measuring a growth rate of the cell in the cell culture, wherein the growth rate of the cell is measured from one of an optical density (OD) of the cell culture or cell doubling rate obtained from one of a cell counter instrument, a microscopic or cytometric method;

creating, via one or more processors, a genome scale metabolic model (GEM) for the cell based on transcriptomic data, metabolomic data or thermodynamic constraints of a cellular organism, wherein the GEM model comprises a biomass function as an objective function, and wherein the measured concentration of the one or more metabolites is incorporated into a combinatorial sink reaction of the GEM, the GEM comprising a combinatorial sink function:

$$v_{accum} = \sum_{i=1}^{m} c_i m_i$$

wherein m is a number of metabolite concentrations measured, m⊆M where M is all the produced metabolites present in the network, $c_i$ is the concentration of the metabolite measured (in mM units) and $v_{accum}$ is a sink function;

calculating, via the one or more hardware processors, a predetermined first percentage value and a predetermined second percentage value of a flux based on the measured growth rate of the cell;

performing, via the one or more hardware processors, a first steady state simulation of the GEM to obtain the flux through a biomass function wherein the biomass function is optimized by applying minimal constraints on reaction fluxes, wherein the minimal constraints are based on predefined input parameters comprising at least one of type and concentration of nutrients, pH, oxygen availability, and antimicrobial treatment, and wherein the obtained flux through biomass function pertains to steady state flux values through all reactions in the GEM;

constraining, via the one or more hardware processors, a lower bound of the biomass function by one of restricting a reaction flux to a predetermined first percentage value of the obtained flux through the biomass function using the first steady state simulation or to the predetermined first percentage value of the flux calculated based on the measured growth rate of the cell;

constraining, via the one or more hardware processors, an upper bound of the biomass function by one of restricting the reaction flux to a predetermined second percentage value of the obtained flux through the biomass function using the first steady state simulation or to the predetermined second percentage value of the flux calculated based on the measured growth rate of the cell;

performing, via the one or more hardware processors, a second steady state simulation to optimize reaction flux through the combinatorial sink reaction;

calculating, via the one or more hardware processors, reaction fluxes through all reactions in the GEM from the second steady state simulation;

determining the metabolic state of the cell based on the calculated fluxes from the second steady state simulation;

determining an effect of uptake of nutrients by the cell in the cell culture on biomass production or production of a biotechnological or a pharmaceutical compound in the cell culture based on the determined metabolic state of the cell; and optimizing one or more reactions in the GEM based on the determined effect of the nutrients' uptake for increasing yield of a biomass, the biotechnological compound or the pharmaceutical compound in the cell culture.

2. The method of claim 1 wherein the concentration of the one or more metabolites is measured from the intracellular and extracellular concentrations of metabolites in the cell culture.

3. The method of claim 2, further comprising the step of converting the measured concentration into normalized per cell count or cell weight milli-Molar units before creating the GEM.

4. The method of claim 1, wherein the combinatorial sink reaction is created based on normalized concentrations of the measured metabolites as their stoichiometric coefficients.

5. The method of claim 1, wherein the cell is one of a eukaryotic cell, a prokaryotic cell, an aggregation of a multitude of prokaryotic or eukaryotic cells or both.

6. The method of claim 1, further comprising the step of constraining, via the one or more hardware processors, a lower bound of the biomass function for a test condition and a control condition, wherein the lower bound is based on a ratio of growth rates of the cell under the test condition and the control condition.

7. The method of claim 1, wherein the predetermined first percentage value of the obtained flux through the biomass function is about 90% and the predetermined second percentage value of the obtained flux through the biomass function is about 110%.

8. The method of claim 1, further comprises determining effect of stress or therapeutics on the cell based on determined metabolic state of the cell.

* * * * *